United States Patent [19]

Mori

[11] Patent Number: 4,699,087
[45] Date of Patent: * Oct. 13, 1987

[54] CONCENTRATED FISH FEEDING DEVICE

[76] Inventor: Kei Mori, 3-16-3-501, Kaminoge, Setagaya-ku, Tokyo, Japan

[*] Notice: The portion of the term of this patent subsequent to Oct. 13, 2004 has been disclaimed.

[21] Appl. No.: 793,028

[22] Filed: Oct. 30, 1985

[30] Foreign Application Priority Data

Nov. 7, 1984 [JP] Japan .................................. 59-234438

[51] Int. Cl.⁴ ............................................. A01K 61/00
[52] U.S. Cl. ........................................... 119/3; 47/1.4
[58] Field of Search .................. 126/440, 425; 362/32; 119/2, 3; 47/1.4, 59; 405/70, 220, 195, 219, 211, 218, 221, 224, 21, 23, 24, 25, 26, 27, 28, 29, 30, 32, 33, 34, 35, 63, 64, 71

[56] References Cited

U.S. PATENT DOCUMENTS

| 2,709,984 | 6/1955 | Marks | 119/3 |
| 3,955,317 | 5/1976 | Gudin | 47/1.4 X |
| 4,086,161 | 4/1978 | Burton | 47/1.4 X |
| 4,324,067 | 4/1982 | Kessler | 47/1.4 |
| 4,340,812 | 7/1982 | Mori | 126/425 |
| 4,459,643 | 7/1984 | Mori | 362/32 |
| 4,501,084 | 2/1985 | Mori | 43/17.5 |

FOREIGN PATENT DOCUMENTS

| 85EP926 | 8/1983 | European Pat. Off. | 47/1.4 |
| 1299164 | 7/1969 | Fed. Rep. of Germany | 47/1.4 |
| 105444 | 6/1985 | Japan | 47/1.4 |
| 1083944 | 4/1984 | U.S.S.R. | 47/1.4 |

Primary Examiner—Robert A. Hafer
Assistant Examiner—Danton DeMille
Attorney, Agent, or Firm—Jordan & Hamburg

[57] ABSTRACT

A concentrated fish feeding device utilizing a solar ray collecting device and a algae cultivating device installed in the sea, lakes, or ponds, etc. The device comprises a culture device for cultivating algae or the like installed in water, a photo-synthesis light source for supplying light rays to the algae culture device, and an illumination light source for entirely illuminating the algae culture device.

5 Claims, 2 Drawing Figures

U.S. Patent
Oct. 13, 1987
4,699,087
FIG.1
FIG.2
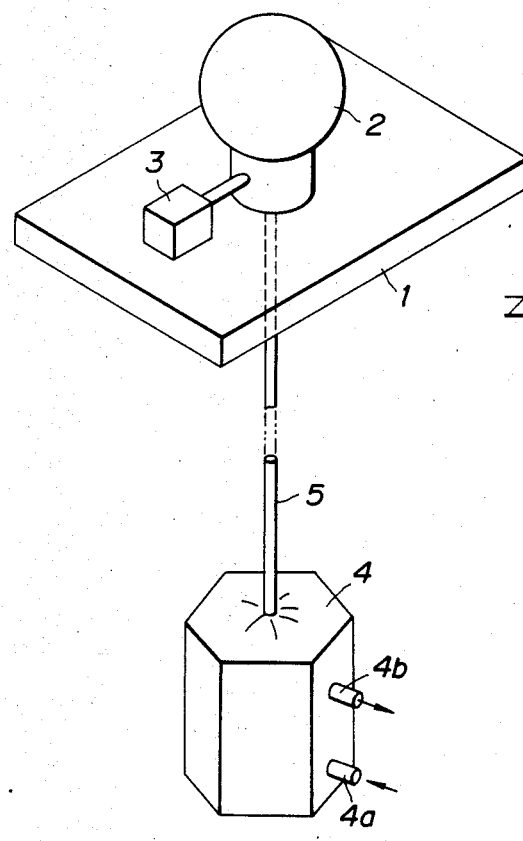
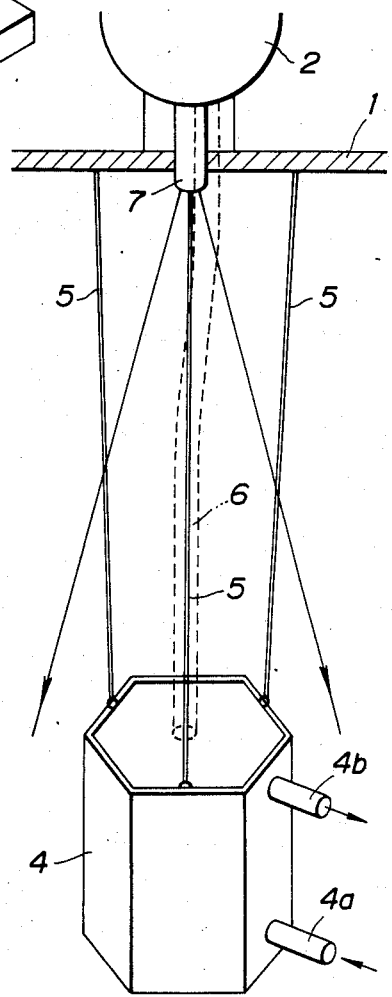

4,699,087

1

CONCENTRATED FISH FEEDING DEVICE

BACKGROUND OF THE INVENTION

The present invention relates to a concentrated fish feeding device, in particular, a concentrated fish feeding device effectively utilizing a solar ray collecting device and an algae cultivating device.

The present applicant has previously proposed various ways to focus solar rays or artificial light rays by use of lenses or the like, to guide the same into an optical conductor cable, and thereby to transmit them onto an optical desired place. The solar rays or the artificial light rays transmitted and emitted in such a way are employed for photo-synthesis and for use in illuminating or for other like purposes, for example, to promote the cultivation of plants or to cultivate algae or the like.

Furthermore, the present applicant has already proposed various culture devices for cultivating algae or the like, for instance, chlorella. Basically, in order to cultivate chlorella, light rays and carbon dioxide $CO_2$ are needed for performing photo-synthesis. By supplying light rays and carbon dioxide $CO_2$ to a chlorella cultivating tub, chlorella is cultivated, and oxygen $O_2$ is created at the same time.

As mentioned above, the solar rays or the artificial light rays are focused by use of lenses or the like and guided into an optical conductor and further guided into the chlorella cultivating tub. Those light rays are radiated from the optical conductor into the chlorella cultivating tub and applied to a desired place. On the other hand, for supplying carbon dioxide $CO_2$ thereto, commercially prepared carbon dioxide $CO_2$ is supplied to the chlorella.

The chlorella produced in such a manner as described above is employed as food for cultivating fish or the like. This method has never been tried until now i.e. where the chlorella cultivating device is installed directly in water and utilized for feeding fish.

SUMMARY OF THE INVENTION

It is an object of the present invention to provide a fish feeding device utilizing a solar ray collecting device.

It is another object of the present invention to provide a fish feeding device utilizing a chlorella cultivating device installed in the sea, lakes, or ponds, etc.

It is another object of the present invention to provide a concentrated fish feeding device possible to improve the water quality in the sea, lakes, or ponds, etc.

It is another object of the present invention to effectively concentrate and feed the fish by use of a chlorella cultivating device installed directly in water and further to improve water quality.

The above-mentioned features and other advantages of the present invention will be apparent from the following detailed description which goes with the accompanying drawings.

BRIEF DESCRIPTION OF THE DRAWINGS

FIG. 1 is a perspective construction view for explaining an embodiment of a concentrated fish feeding device according to the present invention; and FIG. 2 is a construction view for explaining another embodiment of the present invention.

DESCRIPTION OF THE PREFERRED EMBODIMENT

FIG. 1 is a perspective construction view for explaining an embodiment of a concentrated fish feeding device according to the present invention. In FIG. 1, 1 is a floating body in water, 2 a solar ray collecting device installed on the floating body 1, 3 an artificial light source device, including an electric power source such as a generator or a solar battery, 4 a culture device for cultivating the algae or the like such as chlorella, and 5 a wire and/or a cylinder for suspending the chlorella cultivating device 4 from the floating body 1. An optical cable is put along the wire or through the cylinder.

As is well known, the solar ray collecting device 2 focuses solar rays by use of lenses or the like and guides them into the optical conductor cable. The light rays guided into the optical conductor cable in such a manner are supplied to the chlorella cultivating device 4 through the optical conductor cable. In the chlorella cultivating device 4, the light rays are employed as a photo-synthesis light source for cultivating the chlorella.

Furthermore, an artificial light source 3 activated by a solar battery, a storage battery charged by the solar battery and/or a generator are additionally provided. In such a construction, the light rays emitted from the artificial light source are supplied to the chlorella cultivating device through the optical conductor cable. Even when the solar rays are very faint in brightness or cannot be collected at all during the night, the chlorella can still be cultivated in the manner mentioned heretofore.

When the outer circumferential surface of the chlorella cultivating device 4 is constructed with a transparent substance, the light rays employed for cultivating the chlorella will leak from the chlorella cultivating device. Therefore, it not only will gather fish seeking the light rays which leak therefrom, but also the algae will stick to the outer surface of the chlorella cultivating device seeking the same. Since algae is a bait for fish, the fish will eat the algae and grow. The outer circumferential surface of the chlorella cultivating tub will also be cleaned in this manner.

FIG. 2 is a construction view of the main portion of explaining another embodiment of the present invention. In FIG. 2, 5 consists of wires for suspending the chlorella cultivating device 4 from the floating body 1, 6 an optical conductor cable for supplying the light rays emitted from the solar ray collecting device 2 and the artificial light source portion 3 to the chlorella cultivating device 4, and 7 is an optical conductor. When a part of the solar rays or the artificial light rays focused in such a manner as mentioned before are radiated from the upper portion of the chlorella cultivating device through the optical conductor 7 as an illumination light source, a large number of fish are attracted to the device. As a result, fish cultivation can be performed much more effectively.

As is previously proposed by the present applicant in Japanese Patent Application No. 165123/1984, the respective chlorella cultivating device are comprised of an inlet opening 4a for taking in external water and an outlet opening 4b for discharging the cultivated chlorella and/or the oxygen $O_2$ created by cultivating the chlorella. The carbon dioxide $CO_2$ phosphorus, nitrogen, nutritious salt, etc. contained in water are taken into the chlorella cultivating device 4 through the inlet opening 4a in order to cultivate the chlorella, and then the cultivated chlorella and/or the oxygen $O_2$, created by cultivating the chlorella, are discharged back into the water through the outlet opening 4b.

Consequently, it follows that the substance needed for cultivating the chlorella is taken in from the water, the oxygen $O_2$ and the bait needed for feeding the fish are produced in the chlorella cultivating device 4 and discharged back into the sea. Therefore, it may be possible to improve the water's quality and cultivate fish at a lower cost and more effectively.

As is apparent from the foregoing description, according to the present invention, it will be possible to improve the water quality and perform the cultivation of fish more effectively and at the same time, in the sea, in lakes, or in ponds, etc.

I claim:

1. A concentrated fish feeding device comprising a floating body floatable on a body of water, a culture device within said body of water for cultivating algae, suspension means suspending said culture device from said floating body, said suspension means suspending said culture device within said body of water, a solar ray collecting device on said floating body, said solar ray collecting device being disposed above said floating body, optical cable means for transmitting light rays from said solar ray collecting device to said culture device, said culture device comprising a wall of transparent material, said optical means further comprising radiating means for radiating at least some of the light rays transmitted to the culture device by said optical cable means through said transparent material to the surrounding body of water, said culture device having inlet means for introducing into the culture device substances such as carbon dioxide, phosphorus, nitrogen, and nutritious salt from said body of water and utilized for cultivating algae, said culture device further having discharge means for discharging substances such as algae and oxygen into said body of water, whereby the discharged substances are utilized to improve the quality of said body of water and to feed fish in said body of water.

2. A concentrated fish feeding device according to claim 1 wherein said culture device comprises means to cause algae to adhere to the outside thereof to be eaten by fish in the body of water.

3. A concentrated fish feeding device comprising a floating body floatable on a body of water, a culture device within said body of water for cultivating algae, suspension means suspending said culture device from said floating body, said suspension means suspending said culture device within said body of water, a solar ray collecting device on said floating body, said solar ray collecting device being disposed above said floating body, optical cable means for transmitting light rays from said solar ray collecting device to said culture device, said culture device having an outer wall of transparent material, said optical cable means further comprising radiating means by which at least some of the light transmitted by said optical cable means is radiated through said transparent outer wall to the surrounding body of water, said culture device having inlet means for introducing into the culture device substances from the surrounding body of water such as carbon dioxide, phosphorus, nitrogen, and nutritious salt utilized for cultivating algae, said culture device further having discharge means for discharging algae into the surrounding body of water, whereby said culture device thereby cultivates said algae utilizing said transmitted solar rays as a photo-synthesis light source and utilizing carbon dioxide, phosphorus, nitrogen, and nutritious salt contained in said body of water, said algae cultivated by said culture device and discharged into said body of water being used for the feeding of fish and to improve the quality of said body of water.

4. A concentrated fish feeding device according to claim 3 wherein said floating body has support means extending above the floating body and above the level of said body of water, said solar ray collecting device being disposed on said support means above said body of water.

5. A concentrated fish feeding device according to claim 3 wherein said optical conductor cable means radiates light into the surrounding body of water.

* * * * *